US012790403B2

(12) United States Patent
Putics et al.

(10) Patent No.: US 12,790,403 B2
(45) Date of Patent: Nov. 10, 2026

(54) METHOD FOR INCREASING THE GALACTOSE CONTENT OF RECOMBINANT PROTEINS

(71) Applicant: RICHTER GEDEON NYRT., Budapest (HU)

(72) Inventors: Ákos Putics, Budapest (HU); Dénes Zalai, Budapest (HU); Gáspár Nagy, Kecskemét (HU); László Párta, Budapest (HU); Áron Schleicher, Budapest (HU)

(73) Assignee: Richter Gedeon NYRT., Budapest (HU)

( * ) Notice: Subject to any disclaimer, the term of this patent is extended or adjusted under 35 U.S.C. 154(b) by 72 days.

(21) Appl. No.: 17/749,499

(22) Filed: May 20, 2022

(65) Prior Publication Data

US 2022/0372157 A1 Nov. 24, 2022

Related U.S. Application Data

(63) Continuation of application No. 15/749,978, filed as application No. PCT/EP2016/068651 on Aug. 4, 2016, now abandoned.

(30) Foreign Application Priority Data

Aug. 4, 2015 (HU) .................................... P1500363

(51) Int. Cl.
*C12N 5/00* (2006.01)
*C07K 16/28* (2006.01)

(52) U.S. Cl.
CPC ........ *C07K 16/2887* (2013.01); *C12N 5/0018* (2013.01); *C07K 2317/24* (2013.01); *C07K 2317/41* (2013.01); *C07K 2317/734* (2013.01); *C12N 2500/20* (2013.01); *C12N 2500/32* (2013.01); *C12N 2500/34* (2013.01); *C12N 2500/40* (2013.01); *C12N 2510/02* (2013.01)

(58) Field of Classification Search
None
See application file for complete search history.

(56) References Cited

U.S. PATENT DOCUMENTS

2012/0276631 A1 11/2012 Bengea et al.

FOREIGN PATENT DOCUMENTS

| | | | |
|---|---|---|---|
| EP | 2511293 | A1 | 10/2012 |
| WO | WO 92/16553 | | 10/1992 |
| WO | WO 92/22653 | | 12/1992 |
| WO | WO 94/11026 | | 5/1994 |
| WO | WO 97/29131 | | 8/1997 |
| WO | WO 98/45331 | | 10/1998 |
| WO | WO 03/002713 | | 1/2003 |
| WO | WO 2012/149197 | A2 | 11/2012 |
| WO | WO 2014/170866 | A2 | 10/2014 |
| WO | WO 2015/135884 | A1 | 9/2015 |
| WO | WO 2017/021493 | A1 | 2/2017 |

OTHER PUBLICATIONS

DAC (www.phadjustment.com/TArticles/Phosphoric_Acid.html; accessed Mar. 21, 2025, version form Mar. 21, 2013). (Year: 2013).*
Villiger, Bioprocess Engineering Framework to Control Protein N-linked Glycosylation, 2015, ETH Zurich; Phd Thesis; May 2015) (Year: 2015).*
Chartrain, M., et al., "Development and production of commercial therapeutic monoclonal antibodies in Mammalian cell expression systems: an overview of the current upstream technologies," *Curr. Pharm. Biotechnol. 9*(6):447-467, Bentham Science Publishers, Netherlands (2008).
Grainger, R., et al., "CHO cell line specification prediction and control of recombinant monoclonal antibody N-glycosylation," *Biotechnology and Bioengineering 110*(11):2970-2983, Wiley and Sons, United States (2013).
Gramer, M., et al., "Modulation of Antibody Galactosylation Through Feeding of Uridine, Manganese Chloride and Galactose," *Biotechnology and Bioengineering 108*(7):1591-1602, Wiley and Sons, United States (2011).
International Search Report and Written Opinion for PCT/EP2016/068651, mailed Nov. 14, 2016 , European Patent Office, Germany, 17 pages.
Ivarsson, M., et al., "Evaluation the impact of cell culture process parameters on monoclonal antibody N-glycosylation," *Journal of Biotechnology 188*:88-96, Elsevier Science Publishers, Netherlands (2014).
Liu, B., et al., "The availability of glucose to CHO cells affects the intracellular lipid-linked oligosaccharide distribution, site occupancy and the N-glycosylation profile of a monoclonal antibody," *Journal of Biotechnology 170*(25):17-27, Elsevier, Netherlands (2013).

(Continued)

*Primary Examiner* — Maria G Leavitt
*Assistant Examiner* — Alexandra F Connors
(74) *Attorney, Agent, or Firm* — Sterne, Kessler, Goldstein & Fox P.L.L.C.

(57) ABSTRACT

The present invention relates to a method for increasing the galactose content of a recombinant protein produced in mammalian cells, wherein during the cultivation of said cells the pH of the cell culture is changed and a composition comprising nucleosides, transition metal salts and/or sugars is fed.

11 Claims, No Drawings

(56) References Cited

OTHER PUBLICATIONS

Visser, J., et al., "Physicochemical and Functional Comparability between the proposed Biosimilar Rituximab GP2013 and Originator Rituximab," *BioDrugs 27*(5):495-507, Springer, United States (2013).
Boyd, P. N., et al., "The Effect of the Removal of Sialic Acid, Galactose and Total Carbohydrate on the Functional Activity of Campath-1H," *Molecular Immunology 32*(17):1311-1318, Pergamon, Great Britain (1996).
Gazzano-Santoro, H., et al., "A non-radioactive complement-dependent cytotoxicity assay for anti-CD20 monoclonal antibody," *J. Immunol Methods 202*:163-171, Elsevier, Netherlands (1997).
Jefferis, R., "Glycosylation as a strategy to improve antibody-based therapeutics," *Nature Rev. Drug Discover 8*:226-234, Nature Publishing Group, United Kingdom (2009).
McCracken, N. A., et al., "Control of galactosylated glycoforms distribution in cell culture systems," *Biotechnol Prog. 30*(3):547-553, Wiley Online Library, United States (2014).
Fan, Y., et al., "Amino Acid and Glucose Metabolism in Fed-batch CHO Cell Culture Affects Antibody Production and Glycosylation," Biotechnology and Bioengineering 112(3):521-535, Biotechnology & Bioengineering, Wiley Periodicals, United States (2014).
Nahrgang, S., "Influence of Cell-Line and Process conditions on the glycosylation of Recombinant Proteins," Thesis No. 2608, Presented at the Facultte of Sciences de Base, Ecole Polytechnique Federale De Lausanne, Lausanne, Switzerland, 159 pages (2002).
Pacis, E., et al., "Effects of Cell Culture Conditions on Antibody N-linked Glycosylation—What Affects High Mannose 5 Glycoform," Biotechnology and Bioengineering 108(10): 2348-2358, Wiley Periodicals, United States (2011).
Hossler, P., et al., "Optimal and consistent protein glycosylation in mammalian cell culture," *Glycobiology*, 19(9): 936-949, Oxford University Press, United Kingdom (2009).
Müthing, J., et al., "Effects of Buffering Conditions and Culture pH on Production Rates and Glycosylation of Clinical Phase I Anti-melanoma Mouse IgG3 Monocolonal Antibody R24," *Biotechnology and Bioengineering*, 83(3): 321-334, Wiley Periodicals, Inc., New York (2003).
Zhu, M., et al., "Effects of elevated pCO2 and osmolality on growth of CHO cells and production of antibody-fusion protein B1: a case study," *Biotechnol Prog 21*(1):70-77, Wiley, United States (2005).
Kaur, H., "Characterization of glycosylation in monoclonal antibodies and its importance in therapeutic antibody development," Crit Rev Biotechnol 41(2):300-315, Informa Healthcare, United Kingdom (Mar. 2021).

* cited by examiner

METHOD FOR INCREASING THE GALACTOSE CONTENT OF RECOMBINANT PROTEINS

CROSS-REFERENCE TO RELATED APPLICATIONS

This application is continuation of U.S. application Ser. No. 15/749,978, which is a 35 U.S.C. § 371 National Phase Application of International Application No. PCT/EP2016/068651, filed Aug. 4, 2016, which claims the benefit of Hungarian Application No. P1500363, filed Aug. 4, 2015, each of which is hereby incorporated by reference herein in its entirety.

FIELD OF THE INVENTION

The present invention relates to a method for increasing the galactose content of a recombinant protein produced in mammalian cells, wherein during the cultivation of said cells the pH of the cell culture is changed and a composition comprising nucleosides, transition metal salts and/or sugars is fed.

BACKGROUND OF THE INVENTION

In the last 20 years, the use of therapeutic antibodies for the treatment of different diseases such as inflammatory diseases and cancer has become increasingly more important and the first biosimilar antibody products are already marketed.

Naturally occurring antibodies derived from mammalian serum are glycosylated in their constant region and this glycosylation is important for the effector functions of the antibodies such as antibody-dependent cell-mediated cytotoxicity (ADCC) and complement-dependent cytotoxicity (CDC). Also, recombinant monoclonal antibodies produced in eukaryotic cells show a specific glycosylation pattern. In the development of biosimilar therapeutic antibodies care must also be taken that the biosimilar antibody is comparable to the originator product in terms of glycosylation.

Several studies have shown that the galactose content of a recombinant antibody influences the biological activity of said antibody as measured in a complement-dependent cytotoxicity (CDC) assay (Gazzano-Santoro et al. (1997) J. Immunol. Meth. 202: 163; Boyd et al. (1995) Mol. Immunol. 32: 1311-1318; Jefferis (2009) Nature Reviews Drug Discovery 8: 226-234). In view of the role of the galactosylation on the activity and efficacy of glycoproteins, monitoring and controlling the galactosylation level in the glycoprotein composition is critical.

The prior art discloses various methods for modulating the galactosylation profile of a glycoprotein composition.

Gramer et al. (2011) Biotechnol. Bioeng. 108(7): 1591-1602 discloses that antibody galactosylation can be modulated by feeding cells producing said antibody with uridine, manganese chloride and galactose. Similarly, WO 2012/149197 A2 provides a method for controlling galactosylation using a manganese and/or galactose containing cell culture supplement.

Further, EP 2 511 293 A1 describes a method for controlling galactosylation by $pCO_2$ regulation.

In Ivarsson et al. (2014) J. Biotechnol. 188: 88-96 the effect of single and combined chemical and mechanical stress parameters including pH and dissolved oxygen tension on glycosylation is investigated.

WO 2014/170866 A2 discloses a method for increasing the galactose content of recombinant proteins by reducing the temperature during the cell culture process and maintaining the $pCO_2$ level in a specific range.

McCracken et al. (2014) Biotechnol. Prog. 30(3): 547-553 report on an influence of the asparagine and ammonium concentration in the cell culture medium on the galactosylation of recombinant proteins.

Nevertheless, there is still a need for a cell culture process which enables the precise control of protein galactosylation, in particular in the development of biosimilar products where the galactose level of the biosimilar should be comparable to that of the reference product.

SUMMARY OF THE INVENTION

The present inventors have found that a combination of a pH reduction and feeding the mammalian cells with uridine, manganese chloride and galactose increases the galactosylation of a recombinantly produced antibody to a greater extent than the feeding with uridine, manganese chloride and galactose without pH reduction.

Accordingly, the present invention relates to a method for increasing the galactose content of a recombinant protein produced in mammalian cells, said method comprising:

a) culturing mammalian cells transformed with at least one recombinant nucleic acid molecule encoding the recombinant protein in a cell culture medium at a first pH for a first period of time;
b) culturing said mammalian cells in said cell culture medium at a second pH which is different from the first pH for a second period of time; and
c) feeding a composition comprising at least two of the following components:
   (i) one or more nucleoside(s);
   (ii) one or more transition metal salt(s); and
   (iii) one or more sugar(s);

to the culture of (b).

In another embodiment the present invention relates to a method for producing a recombinant protein in mammalian cells, said method comprising:

a) culturing mammalian cells transformed with at least one recombinant nucleic acid molecule encoding the recombinant protein in a cell culture medium at a first pH for a first period of time;
b) culturing said mammalian cells in said cell culture medium at a second pH which is different from the first pH for a second period of time; and
c) feeding a composition comprising at least two of the following components:
   (i) one or more nucleoside(s);
   (ii) one or more transition metal salt(s); and
   (iii) one or more sugar(s)

to the culture of (b);

d) harvesting the cell culture fluid comprising the recombinant protein; and
e) obtaining the recombinant protein.

Preferably, the recombinant protein is produced at large scale.

Also preferably, the mammalian cells are Chinese hamster ovary cells.

In a preferred embodiment the recombinant protein is an Fc-containing protein.

Preferably, the second pH is lower than the first pH and more preferably the second pH is 0.05 to 0.3 pH units lower than the first pH.

Preferably, the nucleoside is uridine and more preferably the concentration of uridine within the composition is 1 to 20 mM.

Preferably, the transition metal salt is manganese (II) chloride and more preferably the concentration of manganese (II) chloride within the composition is 0.002 mM to 0.1 mM.

Preferably, the sugar is galactose and more preferably the concentration of galactose within the composition is 5 mM to 100 mM.

In still another embodiment the present invention relates to a method for producing a rituximab biosimilar antibody in Chinese hamster ovary cells, said method comprising:

a) culturing Chinese hamster ovary cells transformed with one or more recombinant nucleic acid molecules encoding the light and the heavy chain of the antibody in a cell culture medium at a pH of 7.15 for a first period of time;
b) culturing said Chinese hamster ovary cells in a cell culture medium at a pH of 7.00 for a second period of time;
c) feeding a composition comprising the following components:
   (i) 1 to 20 mM uridine;
   (ii) 0.002 mM to 0.1 mM manganese (II) chloride; and
   (iii) 5 mM to 100 mM galactose to the culture of (b);

d) harvesting the cell culture fluid comprising therituximab; and
e) obtaining therituximab.

In still another embodiment the present invention relates to a method for improving the biosimilarity of a therapeutic antibody produced by Chinese hamster ovary cells to its reference antibody, said method comprising the steps of:

a) culturing Chinese hamster ovary cells transformed with one or more recombinant nucleic acid molecules encoding the light and the heavy chain of the therapeutic antibody in a cell culture medium at a pH of 7.15 for a first period of time;
b) culturing said Chinese hamster ovary cells in said cell culture medium at a pH of 7.00 for a second period of time; and
c) feeding a composition comprising the following components:
   (i) uridine;
   (ii) manganese (II) chloride; and
   (iii) galactose to the culture of (b).

In a preferred embodiment the cells are cultured at the first pH until the viable cell density is 4.5 to $6.0\times10^6$ cells/ml.

In another preferred embodiment the cells are cultured at the second pH for 6 to 7 days.

Preferably, the temperature is kept constant during steps (a), (b) and (c).

Also preferably the composition further contains at least one amino acid selected from the group consisting of L-valine, L-cysteine, L-phenylalanine and L-serine.

Preferably, the feeding of step (c) is performed at least twice.

Also preferably the feeding of step (c) is preceded by a feeding step with a composition to which the components (i) and (iii) have not been added.

Preferably, the culture medium in steps (a) and (b) does not contain uridine and galactose.

Also preferably, the composition of step (c) does not contain one or more of thymidine, fructose, mannose, sucrose and N-acetylmannosamine.

Preferably, the osmolality of the culture in steps (a), (b) and (c) is lower than 400 mOsm/kg.

DETAILED DESCRIPTION OF THE INVENTION

Although the present invention will be described with respect to particular embodiments, this description is not to be construed in a limiting sense.

Before describing in detail exemplary embodiments of the present invention, definitions important for understanding the present invention are given. As used in this specification and in the appended claims, the singular forms of “a” and “an” also include the respective plurals unless the context clearly dictates otherwise. In the context of the present invention, the terms “about” and “approximately” denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term “comprising” is not limiting. For the purposes of the present invention the term “consisting of” is considered to be a preferred embodiment of the term “comprising”. If hereinafter a group is defined to comprise at least a certain number of embodiments, this is meant to also encompass a group which preferably consists of these embodiments only. Furthermore, the terms “first”, “second”, “third” or “(a)”, “(b)”, “(c)”, “(d)” etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms “first”, “second”, “third” or “(a)”, “(b)”, “(c)”, “(d)”, “i”, “ii” etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As discussed above, the present invention is based on the finding that a change, preferably a reduction, of the cell culture pH and the feeding of a composition comprising nucleosides, transition metal salts and sugars, preferably of uridine, manganese (II) chloride and galactose, to the cell culture increases the galactose content of a recombinant protein, preferably a recombinant antibody.

The term “increase of galactose content” is intended to mean that the percentage of one or all of the galactosylated isoforms G1F, G1'F and G2F in the recombinant protein is higher when the pH of the cell culture is changed, preferably lowered, and a composition comprising nucleosides, transition metal salts and sugars, preferably a composition comprising uridine, manganese chloride and galactose, is fed to the cell culture compared to the percentage of these isoforms in the same recombinant protein produced by a cell culture which is maintained at constant pH and to which the composition as defined above has not been fed. This increase in the percentage of G1F, G1'F and G2F is accompanied by a decrease of non-galactosylated glycoforms such as G0 and G0F.

The G0F, G1F, G1'F and G2F glycoforms have the following structures:

G2F

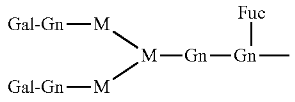

G1F

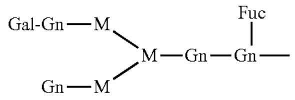

G1'F

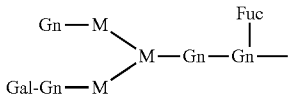

G0F

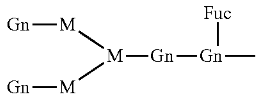

wherein Gn is N-acetylglucosamine; Fuc is fucose; M is mannose and Gal is galactose. These glycan structures are linked to an N-glycosylation site which in the case of IgG1 recombinant antibodies may be located at asparagine 301 of the Cγ2 domain of the Fc region.

The galactose content is increased, if the sum of the percentage of the G1F, G1'F and G2F isoforms in the recombinant protein produced according to the methods of the invention is increased by at least 1%, 2% or 3%, preferably by at least 4%, 5%, 6% or 7%, more preferably by at least 8%, 9% or 10% and most preferably by at least 11% or 12% compared to the sum of the percentage of the G1F, G1'F and G2F iso forms in the same recombinant protein produced by a cell culture which is maintained at constant pH and to which the composition as defined above has not been fed.

The galactose content is also increased, if the percentage of the G0F isoform in the recombinant protein produced according to the method of the present invention is decreased by at least 1%, 2% or 3%, preferably by at least 4%, 5% or 6%, more preferably by at least 7%, 8% or 9% and most preferably by at least 10% compared to the percentage of the G0F isoform in the same recombinant protein produced by a cell culture which is maintained at constant pH and to which the composition as defined above has not been fed.

The galactose content is determined eight to fourteen days after inoculation of the cells into the cell culture medium. In a preferred embodiment, the galactose content is determined nine to ten days after inoculation of the cells into the cell culture medium.

The relative ratio of the different glycan iso forms of the recombinant protein, in particular of the galactosylated isoforms G1F, G1'F and G2F, and consequently of the galactose content can be determined by any method known in the art. Preferably, capillary electrophoresis using laser-induced fluorescence detection (CE-LIF) is used, after the recombinant protein has been deglycosylated and treated with a fluorescence derivatizing agent. The relative content of each of the glycan isoforms is determined by fluorescence detection and calculated using area % values of the corresponding peaks. An exemplary method is described in the Examples section herein below.

The term "inoculation of the cells into the cell culture medium" refers to the step of contacting the cells with the cell culture medium under conditions which are suitable for growth and proliferation of the cells.

The term "recombinant protein" refers to any protein which can be produced by mammalian cell culture as the result of the transcription and translation of a gene encoding said recombinant protein which gene is carried on a recombinant nucleic acid molecule that has been introduced into the mammalian host cell. The recombinant protein may not be produced naturally in the mammalian cells used or the recombinant protein may be produced naturally in the mammalian cells used, but at a lower level. Preferably, the recombinant protein is not produced naturally by the mammalian host cell.

In particular, the term "recombinant protein" encompasses therapeutic proteins such as cytokines, growth factors, clotting factors and antibodies in which the galactose content influences the biological function of the protein. Preferably, the recombinant protein is an Fc containing protein such as an antibody or a fusion protein of the Fc portion of an IgG antibody with parts or all of another protein.

Examples of a fusion protein of the Fc portion of an IgG antibody with parts or all of another protein include etanercept (fusion with TNF receptor), aflibercept (fusion with extracellular domains of VEGF receptors 1 and 2), abatacept (fusion with extracellular domain of CTLA-4) and belatacept (fusion with extracellular domain of CTLA-4).

More preferably, the recombinant protein is a recombinant antibody. The term "recombinant antibody" refers to any antibody which can be produced by mammalian cell culture as the result of the transcription and translation of a gene encoding said recombinant antibody which gene is carried on a recombinant nucleic acid molecule that has been introduced into the mammalian host cell. The recombinant antibody may not be produced naturally in the mammalian cells used or the recombinant antibody may be produced naturally in the mammalian cells used, but at a lower level. Preferably, the recombinant antibody is not produced naturally by the mammalian host cell used for its production.

The terms "immunoglobulin" and "antibody" are used interchangeably herein. The immunoglobulin may be a monoclonal antibody, multispecific antibody (e.g. bispecific antibody) or fragments thereof exhibiting the desired antigen binding activity. Naturally occurring antibodies are molecules with varying structures. For example, native IgG antibodies are heterotetrameric glycoproteins of about 150,000 Daltons, composed of two identical light chains and two identical heavy chains that are linked by disulfide bonds. From N- to C-terminus, each heavy chain has a variable domain (VH), also called a variable heavy domain or a heavy chain variable domain followed by three or four constant domains (CH1, CH2, CH3 and optionally CH4). Similarly, from N- to C-terminus, each light chain has a variable domain (VL), also called a variable light domain or a light chain variable domain followed by a constant light chain (CL) domain. The light chain of an antibody may be assigned to one of two types, called kappa (κ) and lambda (λ), based on the amino acid sequence of its constant domain.

"Antibody fragments" comprise a portion of a full length antibody, generally the antigen binding or variable region thereof. Examples of antibody fragments include Fab, Fab', F(ab')2, and Fv fragments; single-chain antibody molecules; diabodies; linear antibodies; and multispecific antibodies formed from antibody fragments.

Preferably the immunoglobulin is a monoclonal antibody. The term "monoclonal antibody" as used herein refers to an antibody obtained from a population of substantially homogeneous antibodies, i.e. the individual antibodies comprising the population are identical except for possible naturally occurring mutations that may be present in minor amounts. In contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

The immunoglobulin may be of the murine classes IgG1, IgG2a, IgG2b, IgM, IgA, IgD or IgE, the human classes IgG1, IgG2, IgG3, IgG4, IgM, IgA1, IgA2, IgD or IgE, or combinations or fragments thereof.

The immunoglobulin may recognize any one or a combination of proteins including, but not limited to the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, CD152, IL-1a, IL-1B, IL-1, IL-2, IL-3, IL-7, IL-4, IL-5, IL-8, IL-10, IL-12, IL-23, IL-2 receptor, IL-4 receptor, IL-6 receptor, IL-12 receptor, IL-13 receptor, IL-18 receptor subunits, PDGF-β, and analogues thereof, PLGF, VEGF, TGF, TGF-β2, TGF-p1, EGF receptor, PLGF receptor, VEGF receptor, platelet receptor gpIIb/IIIa, thrombopoeitin receptor, apoptosis receptor PD-1, hepatocyte growth factor, osteoprotegerin ligand, interferon gamma, B lymphocyte stimulator BLyS, T-cell activation regulator CTLA-4, C5 complement, IgE, tumor antigen CA125, tumor antigen MUC1, PEM antigen, ErbB2/HER-2, tumor-associated epitopes that are present in elevated levels in the sera of patients, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, α4β1 and α4β7 integrin, TRAIL receptors 1,2,3, and 4, RANK, a RANK ligand (RANKL), TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, sclerostin, MHC I, carcinoembryonic antigen (CEA), alpha-fetoprotein (AFP), tumor necrosis factor (TNF), Fc-y-1 receptor, HLA-DR 10 beta, HLA-DR antigen, L-selectin, and IFN-γ.

The immunoglobulin may for example be afelimomab, abciximab, adalimumab, alemtuzumab, arcitumomab, belimumab, canakinumab, cetuximab, denosumab, trastuzumab, imciromab, capromab, infliximab, ipilimumab, abciximab, rituximab, basiliximab, palivizumab, natalizumab, nivolumab, nofetumomab, omalizumab, daclizumab, ibritumomab, muromonab-CD3, edrecolomab, gemtuzumab, golimumab, certolizumab, eculizumab, ustekinumab, ocrelizumab, ofatumumab, obinutuzumab, panitumumab, pertuzumab, ranibizumab, romosozumab, tocilizumab, tositumomab, clenoliximab, keliximab, galiximab, foravirumab, lexatumumab, bevacizumab, and vedolizumab.

The immunoglobulin of the invention is preferably an IgG molecule, such as an IgG1, IgG2, IgG3, or IgG4 molecule. More preferably, the immunoglobulin is IgG1. Even more preferably, the immunoglobulin is an IgG1 wherein at least the Fc part is human. The immunoglobulin may be a murine-human chimeric IgG1 wherein the Fc part of the IgG1 is human and the variable region is of mouse origin. Most preferably, the chimeric immunoglobulin is rituximab or infliximab.

Rituximab is a chimeric anti-CD20 antibody which is described in detail in, for example, WO 94/11026.

Infliximab is a chimeric anti-TNFα antibody which is described in detail in, for example, WO 92/16553.

The immunoglobulin may be a humanized IgG1 form of a murine progenitor in that the CDRs of the variable domain are derived from mouse and the framework regions of the variable domain are derived from human. Most preferably, the humanized antibody is trastuzumab or bevacizumab.

Trastuzumab is a humanized anti-HER2 antibody which is described in detail in, for example, WO 92/22653.

Bevacizumab is a humanized anti-VEGF antibody which is described in detail in, for example, WO 98/45331.

The immunoglobulin may be a fully human IgG1 antibody, i.e. an antibody in which all parts are derived from human origin. Most preferably the human antibody is adalimumab or denosumab.

Adalimumab is a human anti-TNFα antibody which is described in detail in, for example, WO 97/29131.

Denosumab is a human anti-RANKL antibody which is described in detail in, for example, WO 03/002713.

In one embodiment the antibody may be rituximab or bevacizumab.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired biological activity.

Furthermore, the monoclonal antibodies herein also include "humanized" antibodies. Such antibodies are obtained by "humanization" of non-human (for example murine) antibodies and contain only minimal sequences derived from the animal immunoglobulin. Most of the molecule is comprised of human amino acid sequence. Residues from a hypervariable region of the human recipient antibody are replaced by residues from a hypervariable region of a non-human donor antibody having the desired binding properties.

Finally, the monoclonal antibodies herein also include fully human antibodies which may initially be obtained by screening of a human antibody library.

In the method of the present invention the recombinant protein is produced in mammalian cells. Suitable mammalian host cells for expressing the recombinant antibodies of the invention include Chinese Hamster Ovary (CHO) cells (including dhfr negative CHO cells used with a DHFR selectable marker), NS0 myeloma cells, COS cells, SP2 cells, monkey kidney CV1, human embryonic kidney line 293; baby hamster kidney cells (BHK), mouse Sertoli cells (TM4), African green monkey kidney cells (VERO-76), human cervical carcinoma cells (HELA); canine kidney cells (MDC), buffalo rat liver cells (BRL 3 A), human lung cells (W138), human liver cells (Hep G2), mouse mammary tumor cells (MMT 060562), TRI cells, MRC 5 cells and FS4 cells. Preferably, the host cells are derived from a rodent. More preferably, the mammalian cells are Chinese hamster ovary (CHO) cells, even more preferably the cells are CHO-K1 cells and most preferably the cells are CHO-K1 cells adapted for growth in serum-free media (CHO-S) and/or are obtainable from Invitrogen (Catalogue number R-800-07).

The mammalian cells have been transformed, i.e. genetically modified, with at least one recombinant nucleic acid molecule such as an expression vector which enables the stable production of the recombinant protein in the mammalian host cells.

In the production of recombinant antibodies the mammalian cells may either be transformed with one recombinant nucleic acid molecule which encodes both the heavy and the light chain of the antibody or with two recombinant nucleic acid molecules of which one encodes the light chain of the antibody and the other one encodes the heavy chain of the antibody. In one embodiment, the recombinant antibody is produced from one recombinant nucleic acid molecule which encodes both the heavy and the light chain of the antibody. In a more preferred embodiment, the recombinant antibody is produced from one recombinant nucleic acid molecule and the expression of the heavy and the light chain is controlled by separate promoters which may be the same or different. In a most preferred embodiment, the recombinant antibody is produced from one recombinant nucleic acid molecule and the expression of the heavy and the light chain is controlled by separate promoters which are the same.

The terms “medium”, “cell culture medium” and “culture medium” are interchangeably used herein and refer to a solution containing nutrients which are required for growing mammalian cells. Typically, a cell culture medium provides essential and non-essential amino acids, vitamins, energy sources, lipids, and trace elements required by the cell for minimal growth and/or survival. Preferably, the medium is chemically defined in that all its components and their concentration are known. Also preferably, the medium is serum-free and hydrolysate-free and does not contain any components derived from animals. In a more preferred embodiment the medium is serum-free and hydrolysate-free and does not contain any components derived from animals, but contains HEPES and Pluronic® F-68. In a particularly preferred embodiment the medium used in steps (a) and (b) of the method of the present invention, i.e. the steps before feeding, is PowerCHO-2 CD (available from Lonza under Catalogue number BE12-771Q) which is supplemented with recombinant insulin, lipids, ferric citrate and PEG20000. In the most preferred embodiment the PowerCHO-2 CD medium is supplemented with recombinant insulin, lipids, ferric citrate and PEG20000 and extra amounts of L-tyrosine, L-phenylalanine and L-glutamine. The extra amounts of L-tyrosine, L-phenylalanine and L-glutamine comprise 8 mM L-glutamine, 1.2 mM L-tyrosine and 2 mM L-phenylalanine.

Preferably, no additional amounts of uridine, manganese chloride and galactose have been added to the cell culture medium, but one or more of these components may be present in the basic cell culture medium. Nevertheless, the cell culture medium may contain any or all of these compounds, if they are present in the chemically defined medium used. More preferably, the cell culture medium does not comprise any galactose.

The cell culture medium is preferably subjected to sterile filtration, more preferably to sterile filtration using a filter with 0.1 micron pore size.

The pH of the cell culture medium in step a) of the method of the present invention which is also called “the first pH” is maintained within a range of between pH 7.15 to 7.25, preferably by adding $Na_2CO_3$ or $H_3PO_4$, for a first period of time. The first period of time is 60 to 80 hours, preferably 63 to 79 hours, more preferably 66 to 78 hours and most preferably 70 hours after inoculation of the cell culture medium with the mammalian cells.

After the first period of time, the pH of the cell culture medium is changed, preferably lowered, to a second pH. More preferably, the second pH is 0.05 to 0.3 pH units lower than the first pH and even more preferably, the second pH is 0.15 to 0.25 pH units lower than the first pH. Most preferably, the second pH is pH 7.00. The pH may be lowered by adding a suitable acid or $CO_2$ gas, preferably by adding $H_3PO_4$. The pH is changed when a viable cell density of 4.0 to $7.0\times10^6$ has been reached. The second period of time in which the cells are cultured at the second pH is about 6 to 11 days, or about 6 to 8 days, preferably about seven days. Accordingly, the overall cultivation period in the method of the present invention is eight to fourteen days after inoculation of the cell culture medium with the mammalian cells. Preferably, the overall cultivation period in the method of the present invention is nine to ten days after inoculation of the cell culture medium with the mammalian cells.

In the method of the present invention the cells are fed in step (c) with a composition comprising at least two of the following components: (i) one or more nucleosides, (ii) one or more transition metal salts and (iii) one or more sugars (hereinafter also called components (i) to (iii)), in particular with a composition comprising uridine, manganese chloride and galactose.

The term “feeding” means that the composition is added to the cell culture of step (a) or (b) and no medium or cells is withdrawn during the feeding. The feeding typically does not occur continuously, but at defined time points. In the method of the present invention the composition is fed at defined time points as further detailed below.

The composition which is fed may only comprise components (i) to (iii), e.g. in water or a suitable buffer, or it may be based on a cell culture medium which additionally contains components (i) to (iii). Preferably, the composition which is fed in step (c) of the method is based on a cell culture medium which additionally contains components (i) to (iii). This cell culture medium may be the same or different as the cell culture medium used in the initial culturing of the cells, i.e. after inoculation and before feeding (steps (a) and (b)). Preferably, the cell culture medium used for feeding is different from the one used in the initial culturing of the cells (i.e. steps (a) and (b)). More preferably, the cell culture medium used for feeding is ExCell® of Sigma Aldrich. In another preferred embodiment, the cell culture medium used for feeding is customized salt-free (SF) ExCell® of Sigma Aldrich.

In addition to components (i) to (iii) the cell culture medium used for feeding may also contain other components such as amino acids and other supplements in addition to the basic cell culture medium. Preferably, the cell culture medium used for feeding additionally contains one or more of L-valine, L-cysteine, L-phenylalanine, L-serine and a chemically defined supplement such as BD Recharge. More preferably, the cell culture medium used for feeding comprises L-valine, L-cysteine, L-phenylalanine, L-serine and a chemically defined supplement in addition to components (i) to (iii). Most preferably, the cell culture medium used for feeding is ExCell® or customized salt-free SF ExCell® and comprises L-valine, L-cysteine, L-phenylalanine, L-serine and a chemically defined supplement in addition to components (i) to (iii). The concentration of L-valine in the cell culture medium used for feeding is 34 mM, the concentration of L-cysteine in the cell culture medium used for feeding is 8.3 mM, the concentration of L-phenylalanine in the cell culture medium used for feeding is 4.5 mM and the concentration of L-serine in the cell culture medium used for feeding is 38 mM.

The cell culture medium used for feeding is preferably subjected to sterile filtration, more preferably to sterile filtration using a filter with 0.2 or 0.1 micron pore size.

In another embodiment the composition used for feeding does not contain thymidine, fructose, mannose, sucrose and N-acetylmannosamine.

The composition used for feeding comprises one or more nucleoside(s). Nucleosides are composed of a nitrogenous base and a sugar comprising five carbon atoms such as ribose and desoxyribose. Examples of nucleosides include cytidine, uridine, adenosine, guanosine, thymidine and inosine. Preferably, the nucleoside is uridine.

The concentration of the one or more nucleoside(s) within the composition used for feeding is 1 to 20 mM, preferably 1.5 to 15 mM, more preferably 2 to 12 mM, even more preferably 2.5 to 10 mM and most preferably it is 3 mM. The concentration of uridine within the composition used for feeding is 1 to 20 mM, preferably 1.5 to 15 mM, more preferably 2 to 12 mM, even more preferably 2.5 to 10 mM and most preferably it is 3 mM.

The composition used for feeding further comprises one or more transition metal salt(s). Transition metal salts are salts of a transition metal with a counterion. Transition metals include Fe, Co, Cr, Mn, Mo, Ni, Cu, Zn and suitable counterions include chloride ($Cl^-$), sulphate ($SO_4^{2-}$) and phosphate ($PO_4^{3-}$). Preferably, the transition metal salt is a manganese salt and most preferably it is manganese (II) chloride.

The concentration of the one or more transition metal salt(s) within the composition used for feeding is 0.002 mM to 0.1 mM, preferably 0.005 mM to 0.09 mM, more preferably 0.008 mM to 0.08 mM, even more preferably 0.01 mM to 0.07 mM and most preferably it is 0.06 mM. The concentration of manganese (II) chloride within the composition used for feeding is 0.002 mM to 0.1 mM, preferably 0.005 mM to 0.09 mM, more preferably 0.008 mM to 0.08 mM, even more preferably 0.01 mM to 0.07 mM and most preferably it is 0.06 mM.

The composition used for feeding further comprises one or more sugar(s). Sugars are short-chain carbohydrates and include glucose, fructose, sucrose, galactose, maltose and lactose. Preferably, the sugar is galactose.

The concentration of the one or more sugar(s) within the composition used for feeding is 5 mM to 100 mM, preferably 7.5 mM to 75 mM, more preferably 10 mM to 60 mM, even more preferably 12.5 mM to 50 mM and most preferably it is 15 mM. The concentration of galactose within the composition used for feeding is 5 mM to 100 mM, preferably 7.5 mM to 75 mM, more preferably 10 mM to 60 mM, even more preferably 12.5 mM to 50 mM and most preferably it is 15 mM.

In one embodiment, the concentration of the one or more nucleoside(s) within the composition used for feeding is 1 to 20 mM, the concentration of the one or more transition metal salt(s) within the composition used for feeding is 0.002 mM to 0.1 mM and the concentration of the one or more sugar(s) within the composition used for feeding is 5 mM to 100 mM. In a preferred embodiment, the concentration of one or more nucleoside(s) within the composition used for feeding is 3 mM, the concentration of the one or more transition metal salt(s) within the composition used for feeding is 0.06 mM and the concentration of the one or more sugar(s) within the composition used for feeding is 15 mM.

In one embodiment, the concentration of uridine within the composition used for feeding is 1 to 20 mM, the concentration of manganese (II) chloride within the composition used for feeding is 0.002 mM to 0.1 mM and the concentration of galactose within the composition used for feeding is 5 mM to 100 mM. In a preferred embodiment, the concentration of uridine within the composition used for feeding is 3 mM, the concentration of manganese (II) chloride within the composition used for feeding is 0.06 mM and the concentration of galactose within the composition used for feeding is 15 mM.

The cell culture is fed with the composition comprising components (i) to (iii) at least once, preferably at least twice, more preferably it is fed twice. The feeding with the composition comprising components (i) to (iii) preferably occurs four to six days after the inoculation of the cell culture medium with the cells, more preferably it occurs five days after the inoculation of the cell culture medium with the cells. If the feeding with the composition comprising components (i) to (iii) is performed twice, the first feeding with the composition comprising components (i) to (iii) is performed four to six days, preferably five days, after the inoculation of the cell culture medium and the second feeding with the composition comprising components (i) to (iii) is performed six to eight days, preferably seven days, after the inoculation of the cell culture medium. More preferably, the first feeding with the composition comprising components (i) to (iii) is performed five days after inoculation and the second feeding with the composition comprising components (i) to (iii) is performed seven days after inoculation.

In the first feeding step the composition comprising components (i) to (iii) is diluted by a factor of 8.5 to 10.5, preferably by a factor of 9.0 to 10.0 and most preferably by a factor of 9.3. In the second feeding step the composition comprising components (i) to (iii) is diluted by a factor of 9.5 to 11.5, preferably by a factor of 10.0 to 11.0 and most preferably by a factor of 10.3.

Preferably, the one or more steps of feeding with the composition comprising components (i) to (iii) are preceded by a feeding step with a composition to which the components (i) to (iii) have not been added, but which is otherwise identical to the composition comprising components (i) to (iii). The feeding with a composition to which the components (i) to (iii) have not been added, but which is otherwise identical to the composition comprising components (i) to (iii) takes place two to four days, preferably three days, after the inoculation of the cell culture medium.

Accordingly, the method of the present invention preferably comprises the following feeding steps:

c1) feeding with a composition to which components (i) to (iii) have not been added on day 3 after inoculation;

c2) feeding with a composition to which components (i) to (iii) have been added on day 5 after inoculation; and c3) feeding with a composition to which components (i) to (iii) have been added on day 7 after inoculation.

In the method of the present invention the temperature of the cell culture, i.e. the cell culture medium comprising the mammalian cells, is preferably kept constant during the whole culturing process, meaning that the temperature is not actively up- or down-regulated in the process and that always the same preset temperature is used. Nevertheless, minor variations of the temperature may occur during the culturing process. Preferably, the temperature during the culturing process is set to 36° C. to 38° C. and more preferably the temperature is set to 37° C.

In the process of the present invention the osmolality is preferably lower than 400 mOsm/kg throughout the whole process, i.e. steps (a) to (c), as defined in the claims. Preferably, the osmolality is in the range of 250 to 400 mOsm/kg, more preferably in the range of 300 to 380 mOsm/kg and most preferably in the range of 330 to 370 mOsm/kg. The term "osmolality" as used herein is defined as osmoles of solute per kilogram of solvent and may include ionized or non-ionized molecules. A low osmolality such as an osmolality lower than 400 mOsm/kg can be maintained by using media with a low salt concentration. In particular, the composition used for feeding contains a low salt concentration or contains no salt other than the transition metal salt used in feeding step c) at all.

In the process of the present invention the cells are cultured under aerobic conditions, i.e. a level of dissolved oxygen of 50±40%. The level of carbon dioxide is maintained within a range of between 0 to 90 mmHg, optionally by adjusting the mixing rate or the intensity of aeration.

The process of the present invention is performed without glucose limitation. Accordingly, glucose is added to the cell culture to keep the glucose level in the range of 5 to 35 mM, preferably in the range of 10 to 25 mM.

If foaming of the cell culture occurs, antifoam agent may be added to the culture at any time during the process of the present invention.

After the recombinant protein has been produced according to the method of the present invention the product is harvested. Since recombinant proteins, in particular antibodies, expressed from mammalian cells are typically secreted into the cell culture fluid during the cultivation process, the product harvest at the end of the cultivation process occurs by separating cell culture fluid comprising the recombinant protein from the cells. The cell separation method should be gentle to minimize cell disruption to avoid the increase of cell debris and release of proteases and other molecules that could affect the quality of the immunoglobulin product. Usually, the harvesting of the cell culture fluid comprising the recombinant protein involves centrifugation and/or filtration, whereby the recombinant protein is present in the supernatant and the filtrate, respectively. Expanded bed adsorption chromatography is an alternative method to avoid centrifugation/filtration methods.

After harvesting the cell culture fluid comprising the recombinant protein the recombinant protein has to be purified from the cell culture fluid. The purification of recombinant proteins and in particular recombinant antibodies is usually accomplished by a series of chromatographic steps such as anion exchange chromatography, cation exchange chromatography, affinity chromatography, hydrophobic interaction chromatography, hydroxyapatite chromatography and size exclusion chromatography. Further, the purification process may comprise one or more ultra-, nano- or diafiltration steps. One particularly suitable method which is described in PCT/EP2015/054862 involves the steps of anion exchange chromatography in the flow-through mode, affinity chromatography on a protein A resin and cation exchange chromatography in the bind-and-elute mode.

The processes of the present invention are suitable for producing the recombinant protein at large scale, meaning in a culture volume of at least 500 or 1.000 liters, preferably at least 5.000 or 8.000 liters and most preferably of 10.000 or 20.000 liters.

The process of the present invention improves the biosimilarity of a biosimilar therapeutic antibody to its reference product, i.e. the marketed therapeutic antibody. A biosimilar therapeutic antibody is a therapeutic antibody which is marketed after the patent protection for the original product has expired and which has the same amino acid sequence as the original product, but may slightly differ in posttranslational modifications. Nevertheless, they show a physiological effect which is identical to that of the original product. When an application for a marketing authorisation for a biosimilar of a marketed antibody is filed, it has to be shown that the structure of the biosimilar antibody is comparable to the reference product. One important parameter for assessing biosimilarity of glycosylated proteins is the glycosylation pattern which may influence the effector functions of the antibody.

By using the method of the present invention the glycosylation pattern and in particular the galactose level of the biosimilar antibody is comparable to that of the reference product, thereby improving the biosimilarity compared to the glycosylation pattern and the biosimilarity of a therapeutic antibody which has not been subjected to a pH reduction, and which has not been fed with a composition comprising uridine, manganese (II) chloride and galactose.

The following examples and figures are provided for illustrative purposes. It is thus understood that the examples and figures are not to be construed as limiting. The skilled person in the art will clearly be able to envisage further modifications of the principles laid out herein.

Examples

The method of the present invention is supported and illustrated by reference to the following non-limiting examples.

The selected experiments presented in the following tables were performed with rituximab, a mouse-human chimeric, anti-CD20, IgG1 antibody, which was recombinantly expressed in CHO cells propagated in fed-batch cultures of different scales. In the examples this antibody is also called the model antibody.

However, the invented methods do neither depend on specific antibodies nor on specific host cells used for the expression of the immunoglobulins. The same is true for the mode of expression and the selected culture conditions, which were optimized in terms of protein galactosylation profile and maximum yields in the harvest.

1. Methods

1.1 Cell Culture

Cells

Chinese Hamster Ovary Cell line S (CHO-S), derived from a commercially available suspension-preferring subclone of the common CHO K1 cell line, adapted to growth in serum-free media and originally selected for its superior growth (incl. less aggregation in agitated culture) and transfection efficiency was purchased from Invitrogen (Cat. No.:

R-800-07, Lot. 1335750). The CHO-S cells were adapted to growth in serum-free, chemically-defined PowerCHO-2 medium (Lonza Inc US).

Fed-Batch Culture

CHO cells genetically engineered to express the model antibody were grown initially in basal media PowerCHO-2 (Lonza). On every second day from the 3rd day (post inoculation) of cultivation on three times concentrated (3×) ExCell feed (37 g/L; SAFC) at a feed to initial working volume (volume of the basal medium plus inoculum) ratio of 15% was added to the culture in shot-wise mode.

Suppliers and Catalogue Numbers of media and additional supplements utilized in the examples are summarized below:

| | |
|---|---|
| PowerCHO-2 CD | Lonza, Cat. No.: BE12-771Q |
| ExCell ® CD CHO Fusion | SAFC, Cat. No.: 24365C |
| SF ExCell ® CD CHO Fusion | SAFC, customized |
| L-glutamine | Gibco, Cat. No.: 25030<br>Sigma-Aldrich, Cat No.: G5792 |
| L-proline (Pro; L-Pro) | Sigma-Aldrich, Cat No.: P8865 |
| L-valine (Val; L-Val) | Sigma-Aldrich, Cat No.: V4638 |
| L-cysteine (Cys; L-Cys) | Sigma-Aldrich, Cat No.: C5360 |
| L-phenylalanine (Phe; L-Phe) | Sigma-Aldrich, Cat No.: P8740 |
| L-tyrosine (Tyr; L-Tyr) | Sigma-Aldrich, Cat No.: T4321 |
| L-serine (Ser; L-Ser) | Sigma-Aldrich, Cat No.: S1315 |
| BD Recharge ™ Supplement | Becton-Dickinson Biosciences,<br>Cat. No.: 670002 |
| Uridine | Sigma-Aldrich, Cat. No.: U3003 |
| Manganese(II) chloride solution | Sigma-Aldrich, Cat. No.: M1787 |
| β-D-Galactose | Sigma-Aldrich, Cat. No.: G5388 |

The cultivation temperature was maintained at 37° C. The pH was kept in the range of between pH 7.05 and pH 7.15 by addition of 0.5 M $Na_2CO_3$ or $H_3PO_4$. Dissolved oxygen (DO) set point was 40%. The relevant metabolites were measured every day. The glucose level was maintained at about 20 mM. Cells were cultivated for between 9 to 10 days.

The experiments were mainly performed with harvested culture fluid from a laboratory scale of 1, 5, 10 or 100 L. The production scale and maximum culture volume used in the examples was 1000 L. If not specified otherwise, the scale always refers to the culture volume.

1.2 Purification

Protein A Chromatography

For quality analysis, the obtained model antibody was affinity purified from the fermentation broth using Protein A chromatography. This capture offers an exceptional selectivity for Fc-bearing molecules, thereby removing more than 99.5% of contaminants in a single step.

1.3 Analytics

Viable Cell Density and Viability

Viable cell density and cell viability were determined by Countess™ Automated Cell Counter (Invitrogen Carlsbad, CA, 2008) using the Trypan blue staining method.

Glucose

Glucose concentration was measured with Accu-Chek blood glucose meter (Roche, Mannheim, Germany).

pCO2

Dissolved carbon-dioxide content (pCO2) was determined with the ABL80 blood gas analyzer (Radiometer, Bronshoj, Denmark).

pH Measurement

At-line pH measurement for in situ pH meter re-calibration was performed with a S47 SevenMulti pH meter (Mettler Toledo, Zurich, Switzerland).

Osmolality

Osmolality of the samples was determined with Advanced Model 2020 multi-sample osmometer (Advanced Instruments, Norwood, Mass.).

Titer

Protein titer of the (in-process) samples was determined by Protein A affinity HPLC.

Glycosylation Profile

Determination of the relative ratio of a glycan population expressed in migration time corrected area % of glycan forms was performed by capillary electrophoresis using laser-induced fluorescence detection (CE-LIF). Protein samples (200 μg) were deglycosylated by incubation with PNGase-F for 3 hours at 37° C. Precipitation of proteins was performed using chilled ethanol, followed by drying. Reductive amination using fluorescent derivatizing agent 9-Aminopyrene-1,4,6-trisulfonic acid (APTS) and sodium cyanoborohydride was followed by heating for 90 minutes at 55° C. Samples were quenched, and electrophoresed using a CE-LIF system equipped with a 488 nm solid state laser. The relative content of glycans was determined by fluorescent detection. The amount of the released glycans was calculated using Area % values of the corresponding peaks. The four main glycans of the model antibody (G0F, G1F, G1'F, G2F) were evaluated for release and stability testing. Acceptance criteria were: G0F: 40-56 area %; G1F: 28-38 area %; G1'F: 9-13 area % and G2F: 5-12 area %.

Separation parameters included:

Capillary diameter of 50 μM I.D.

Capillary length:total length (Lt)=50.2 cm

Length to detector (Ld)=40.2 cm

Neutral Capillary

PEO Gel 20 minute run time

Capillary temperature 20° C.

Sample Storage Temperature 10° C.

Bioactivity

The bioactivity of the model antibody was determined using the complement-dependent cytotoxicity (CDC) assay. The basis of the CDC method is that the model antibody binds in a specific manner to its antigen expressed on the surface of the target cells; the thus formed antigen-antibody complex activates the complement system, as a result of which the cells die in a dose-dependent manner. Surviving cells are detected by the addition of AlamarBlue® reagent. The evaluation of CDC assay is based on the comparison of the sigmoid dose-response curves obtained for the dilution series of both the sample and the reference.

2. Results

2.1 Optimization of Osmolality

For optimization of the feed composition according the cell's nutritional requirements, the impact of osmolality of the feed composition on protein glycoforms/galactosylation of the model antibody produced by CHO cells was analyzed in 1 L fed-batch fermentation experiments.

CHO cells genetically engineered to express the model antibody were grown initially in basal media (PowerCHO-2, Lonza Inc US). On every second day from the 3rd day (post inoculation) on 15% 3× concentrated ExCell feed (37 g/L; SAFC) was added to the culture in shot-wise mode.

Table 1 shows the medium supplementation during the respective experiments.

TABLE 1

Feeding strategy used during the fed-batch fermentation runs A and B

| Experiment | Feeding strategy | Basal medium + Feed |
|---|---|---|
| A | Basal Medium + 1 amino acid;<br>15% (3x) ExCell feed + 4 amino acids | Basal medium: PowerCHO-2 CD + 8 mM Gln<br>Basal feed: 15% (37 g/L) 3x ExCell CD on Day 3, 5, 7, 9 . . .<br>Supplementation: Pro, Cys, Val, Phe on day 3, 5, 7, 9 . . . |
| B | Basal Medium + 2 amino acids;<br>15% (3x) SF ExCell feed + 6 amino acids | Basal medium: PowerCHO-2 CD + 8 mM Gln + Tyr + Phe<br>Basal feed: 15% (37 g/L) 3x SF ExCell CD on day 3, 5, 7, 9 . . .<br>Supplementation: Pro, Cys, Val, Phe, Ser on day 3, 5, 7, 9 . . . ;<br>Tyr (3x cc.) only on day 5 |

The cultivation temperature was maintained at 37° C. The pH was kept in the range of between pH 7.05 to pH 7.15 by addition of 0.5 M $Na_2CO_3$ or $H_3PO_4$. Dissolved oxygen (DO) set point was 40%. The relevant metabolites were measured every day. The glucose level was maintained at about 20 mM. Cells were cultivated for between 9-10 days.

The glycosylation pattern was analyzed daily from samples of the fermentation broth from the 3rd day (post inoculum) of cultivation on. For quality analysis, the obtained antibody was affinity purified from the fermentation broth using protein A. Cell viability, titer and osmolality were assessed daily from the 3rd day post inoculum of cultivation on.

The bioactivity of the obtained antibody was determined using the complement-dependent cytotoxicity (CDC) assay.

While monitoring metabolites and ensuring adequate nutrient levels at constant pH, DO, stirring speed, and temperature, the osmolality was consistently increasing during the cultivation reaching up to 650 mOsm/kg in the later phases of cultivation while viable cell density steadily decreased.

Table 2 shows on the basis of several results of samples from fed-batch experiments that increasing osmolality led to a significantly poorer glycosylation pattern implying that an osmolality of higher than 400 mOsm/kg may have a negative impact on protein glycosylation. Due to the accumulation of salts in the culture, the amount of non-galactosylated forms (G0F) was increasing, while the amount of the galactosylated forms was decreasing. Analogously, bioactivity of the respective antibody samples according to a CDC Assay was decreasing with increasing osmolality of the fermentation broth.

TABLE 2

Effect of osmolality fermentation parameter on galactosylation

| | Final Osmolality [mOsm/kg] | G0F [%] | G1F [%] | G1'F [%] | G2F [%] | CDC Rel. Pot. |
|---|---|---|---|---|---|---|
| Reference* | — | 40-56 | 28-38 | 9-13 | 5-12 | 1.0 |
| | 350 | 40.7 | 39.5 | 11.4 | 8.5 | 1.1 |
| | 369 | 49.0 | 33.8 | 10.0 | 7.1 | 0.9 |
| | 405 | 47.6 | 34.5 | 10.6 | 7.3 | 1.1 |
| | 430 | 50.8 | 32.5 | 9.7 | 7.0 | 1.0 |
| | 439 | 51.0 | 31.8 | 9.9 | 7.2 | 0.9 |
| | 570 | 51.2 | 32.2 | 10.1 | 6.5 | 0.8 |
| | 618 | 56.6 | 29.2 | 9.4 | 4.6 | 0.7 |

*calculated from the mean and standard deviation of the glycosylation profiles of 13 commercially available antibody batches.

As the three times concentrated salt-containing ExCell feed contributed to the high osmolality of the cell culture, the original ExCell feed composition was modified to contain 66% less sodium phosphate compared to the original medium.

The antibody glycosylation pattern after 10 days of cultivation (post inoculum) from fed-batch fermentation runs A and B is shown in Table 3.

TABLE 3

Effect of osmolality fermentation parameter on galactosylation

| Experiment | Osmolality [mOsm/kg] | G0F [%] | G1F [%] | G1'F [%] | G2F [%] | CDC Rel. Pot. |
|---|---|---|---|---|---|---|
| Reference* | | 40-56 | 28-38 | 9-13 | 5-12 | 1.0 |
| A | 618 | 56.6 | 29.2 | 9.4 | 4.6 | 0.7 |
| B | 369 | 49.0 | 33.8 | 10.0 | 7.1 | 0.9 |

*calculated from the mean and standard deviation of the glycosylation profiles of 13 commercially available antibody batches.

An osmolality below 400 mOsm/kg due to the customized salt free ExCell feed used in fed-batch fermentation run B had a positive impact on the antibody glycosylation pattern, e.g. a reduction of non-galactosylated glycoforms and an increase in galactosylated glycoforms and CDC activity compared to the fed-batch fermentation run A performed with the salt containing ExCell feed.

2.2 Optimization of Galactosylation Through Feed Supplementation with UMG in Combination with Alteration of Cultivation pH The galactosylation pattern of the obtained antibody was investigated after UMG feed and slight pH shift at different time points of the application of the pH shift using the AMBR (Advanced Microscale Bioreactor) system of TAP Biosystems, UK, which is a high-throughput down-scale fermentation platform that mimics the characteristics of bench-top bioreactors in microscale.

Methods

CHO cells genetically engineered to express the model antibody were cultivated for 9 days in basal medium (PowerCHO-2, Lonza Inc US). On every second day from the 3rd day (post inoculation) on 15% (3×) SF ExCell feed (37 g/L; SAFC) supplemented according to Experiment B (Example 2.1, Table 1 with the exception of Proline) was added to the culture in shot-wise mode. UMG supplement (3 mM uridine, 0.06 mM manganese (II) chloride and 15 mM galactose) was added on days 5 and 7 (post inoculation) of cultivation together with the customized SF ExCell feed.

The cultivation pH was kept at pH 7.15 by addition of 0.5 M $Na_2CO_3$ or $H_3PO_4$ until day 3 (post inoculum) of cultivation. Shifts towards pH 7.00 were performed at different time points between 65th-78th hours after inoculation, at a viable cell density of between 4.0-7.0×$10^6$ cells/mL by addition of $H_3PO_4$.

The galactosylation pattern of the produced antibody was analysed with capillary electrophoresis from the crude purified protein.

The effect of cultivation pH on the galactosylation pattern of the obtained antibody samples is summarized in Table 4.

TABLE 4

Antibody galactosylation depending on cultivation pH.

| pH until day 3 | pH from day 3 | Initial Osmolality [mOsm/kg] | Osmolality adjustment | Galactosylation [%] G0F | G1F | G1'F | G2F |
|---|---|---|---|---|---|---|---|
| | | Reference* | | 40-56 | 28-38 | 9-13 | 5-12 |
| 7.15 | 7.15 | 355 | no | 52.0 | 31.0 | 10.8 | 6.3 |
| 7.15 | 7.00 | 355 | no | 47.0 | 34.1 | 11.3 | 7.6 |
| 7.15 | 7.15 | 409 | NaCl | 57.7 | 27.9 | 9.8 | 4.7 |
| 7.15 | 7.00 | 409 | NaCl | 52.7 | 30.9 | 10.5 | 5.9 |

*calculated from the mean and standard deviation of the glycosylation profiles of 13 commercially available antibody batches.

The slight shift from pH 7.15 to pH 7.00 on the 3rd day of cultivation (post inoculation) already had an impact on the glycosylation of the antibody compared to the control, where pH 7.15 was kept constant during cultivation. The percentage of non-galactosylated glycoforms (G0F) could be reduced and the percentage of the galactosylated glycoforms G1F, G1'F and G2F was increased following the pH shift. This positive effect of the slight pH shift on antibody galactosylation could even be observed at osmolalities above 400 mOsm/kg as adjusted in the respective samples by medium supplementation with NaCl. Nevertheless, the osmolality of above 400 mOsm/kg resulted in a significantly poorer glycosylation pattern of the respective antibodies.

Table 5 shows the percental distribution of the, G0F, G1F, G1'F and G2F galactosylation of the obtained antibody samples on days 8 and 9 of cultivation (post inoculum), respectively, and the time point when the pH shift was applied.

TABLE 5

Antibody galactosylation pattern following the combination of UMG feed and pH shift at different time points of pH change.

| | G0F Day 8 | G0F Day 9 | G1F Day 8 | G1F Day 9 | G1'F Day 8 | G1'F Day 9 | G2F Day 8 | G2F Day 9 |
|---|---|---|---|---|---|---|---|---|
| control pH 7.15 | 43.45 | 44.66 | 31.43 | 30.13 | 10.57 | 10.16 | 6.96 | 6.48 |
| pH-shift (66 hr) | 39.83 | 42.12 | 33.29 | 31.04 | 10.80 | 10.15 | 7.94 | 7.03 |
| pH-shift (70 hr) | 38.75 | 42.24 | 34.12 | 31.27 | 11.10 | 10.27 | 8.35 | 7.10 |
| pH-shift (74 hr) | 41.31 | 41.94 | 32.54 | 31.51 | 10.62 | 10.33 | 7.61 | 7.19 |
| pH-shift (78 hr) | 42.18 | 42.92 | 32.05 | 31.00 | 10.60 | 10.24 | 7.38 | 6.92 |

The analysis of the galactosylation pattern on the $8^{th}$ day of cultivation shows a decrease in the percental amount of non-galactosylated glycoform G0F compared to the control samples, where pH 7.15 was kept constant during fermentation. The combination of pH shift and UMG feed resulted in an increase of the percental amount of galactosylated glycoforms (G1F, G1'F and G2F) of the obtained antibody.

As can be seen in Table 6 the feed of UMG alone had a positive impact on antibody galactosylation on day 7 of cultivation (post inoculation) compared to the control without the addition of UMG. However, a significant decrease of the percental amount of non-galactosylated glycoforms and a significant increase of the percental amount of galactosylated glycoforms of the obtained antibody was achieved only when both features (slight pH shift+feed supplementation with UMG) were combined.

TABLE 6

Effect of combination of pH shift and UMG feed on antibody galactosylation

| | Set-up | | | | |
|---|---|---|---|---|---|
| Reference* | Process time [h] | G0F [%] 40-56 | G1F [%] 28-38 | G1'F [%] 9-13 | G2F [%] 5-12 |
| pH 7.15 w/o UMG | 168.00 | 55.31 | 29.04 | 10.12 | 5.53 |
| pH 7.15 + UMG | 168.00 | 50.41 | 32.12 | 10.99 | 6.48 |
| Shift: pH 7.15 to pH 7.0 + UMG | 168.00 | 47.41 | 33.95 | 11.31 | 7.34 |

*calculated from the mean and standard deviation of the glycosylation profiles of 13 commercially available antibody batches.

Altogether, the analysis of the glycosylation pattern of the obtained antibody samples showed that the improved feeding strategy comprising supplementation with UMG on days 5 and 7 (post inoculation) of cultivation in combination with a slight pH shift from pH 7.15 towards pH 7.00 resulted in increased antibody galactosylation.

The invention claimed is:

1. A method for increasing the galactose content of an IgG recombinant antibody produced in Chinese hamster ovary cells, said method comprising:

a) culturing Chinese hamster ovary cells transformed with at least one recombinant nucleic acid molecule encoding the IgG recombinant antibody in a cell culture medium at a first pH of 7.15, which is maintained by adding $Na_2CO_3$ or $H_3PO_4$, for a first period of time until the viable cell density is 4.5 to $6.0\times10^6$ cells/ml, wherein the first period of time is 60 to 80 hours;

b) lowering the pH of the culture medium to a second pH of 7.00 by adding $H_3PO_4$;

c) culturing said Chinese hamster ovary cells in said cell culture medium at said second pH, for a second period of time, wherein the Chinese hamster ovary cells are cultured at the second pH for 6 to 7 days; and d) feeding a composition comprising the following components to the cell culture of step (c):

(i) one or more nucleoside(s), wherein one of the nucleosides is uridine and the concentration of uridine within the composition is 1.5 mM to 15 mM;

(ii) one or more transition metal salt(s), wherein one of the transition metal salts is manganese (II) chloride and the concentration of manganese (II) chloride within the composition is 0.005 mM to 0.09 mM; and (iii) one or more sugar(s), wherein one of the sugars is galactose and the concentration of galactose within the composition is 7.5 mM to 75 mM, wherein feeding with the composition comprising components (i) to (iii) of step (d) occurs four to six days after the inoculation of the cell culture medium with the cells; and, wherein the feeding of step (d) is preceded by a feeding step with a composition to which the components (i) to (iii) have not been added on day 3 after inoculation.

2. A method for producing an IgG recombinant antibody in Chinese hamster ovary cells, said method comprising:

a) culturing Chinese hamster ovary cells transformed with at least one recombinant nucleic acid molecule encoding the IgG recombinant antibody in a cell culture medium at a first pH of 7.15, which is maintained by adding $Na_2CO_3$ or $H_3PO_4$, for a first period of time until the viable cell density is 4.5 to $6.0\times10^6$ cells/ml, wherein the first period of time is 60 to 80 hours;

b) lowering the pH of the culture medium to a second pH of 7.00 by adding $H_3PO_4$;

c) culturing said Chinese hamster ovary cells in said cell culture medium at said second pH, for a second period of time, wherein the Chinese hamster ovary cells are cultured at the second pH for 6 to 7 days; and d) feeding a composition comprising the following components to the cell culture of step (c):

(i) one or more nucleoside(s), wherein one of the nucleosides is uridine and the concentration of uridine within the composition is 1.5 mM to 15 mM;

(ii) one or more transition metal salt(s), wherein one of the transition metal salts is manganese (II) chloride and the concentration of manganese (II) chloride within the composition is 0.005 mM to 0.09 mM; and (iii) one or more sugar(s), wherein one of the sugars is galactose and the concentration of galactose within the composition is 7.5 mM to 75 mM, wherein feeding with the composition comprising components (i) to (iii) of step (d) occurs four to six days after the inoculation of the cell culture medium with the cells; and, wherein the feeding of step (d) is preceded by a feeding step with a composition to which the components (i) to (iii) have not been added on day 3 after inoculation; e) harvesting the cell culture fluid comprising the IgG recombinant antibody; and f) obtaining the IgG recombinant antibody.

3. The method according to claim 2, wherein the IgG recombinant antibody is produced at large scale.

4. The method according to claim 1, wherein the IgG recombinant antibody is an Fc-containing antibody.

5. A method for producing a rituximab biosimilar antibody in Chinese hamster ovary cells, said method comprising:

a) culturing Chinese hamster ovary cells transformed with one or more recombinant nucleic acid molecules encoding the light and the heavy chain of the rituximab biosimilar antibody in a cell culture medium at a pH of 7.15, which is maintained by adding $Na_2CO_3$ or $H_3PO_4$, for a first period of time until the viable cell density is 4.5 to $6.0\times10^6$ cells/ml, wherein the first period of time is 60 to 80 hours;

b) lowering the pH of the culture medium to a second pH of 7.00 by adding $H_3PO_4$;

c) culturing said Chinese hamster ovary cells in a cell culture medium at said second pH for a second period of time, wherein the Chinese hamster ovary cells are cultured at the second pH for 6 to 7 days;

d) feeding a composition comprising the following components to the cell culture of step (c):

(i) 1 to 20 mM uridine;

(ii) 0.002 mM to 0.1 mM manganese (II) chloride; and (iii) 5 mM to 100 mM galactose, wherein feeding with the composition comprising components (i) to (iii) of step (d) occurs four to six days after the inoculation of the cell culture medium with the cells; and, wherein the feeding of step (d) is preceded by a feeding step with a composition to which the components (i) to (iii) have not been added on day 3 after inoculation; e) harvesting a cell culture fluid comprising the rituximab biosimilar antibody; and f) obtaining the rituximab biosimilar antibody.

6. The method according to claim 1, wherein temperature is kept constant during steps (a), (b), (c) and (d).

7. The method according to claim 1, wherein the composition of step (d) of claim 1 further contains at least one amino acid selected from the group consisting of L-valine, L-cysteine, L-phenylalanine and L-serine.

8. The method according to claim 1, wherein the feeding of step (d) is performed at least twice.

9. The method according to claim 1, wherein the culture medium in steps (a), (b) and (c) does not contain uridine and galactose.

10. The method according to claim 1, wherein the composition of step (d) does not contain one or more of thymidine, fructose, mannose, sucrose and N-acetylmannosamine.

11. The method according to claim 1, wherein the osmolality of the culture in steps (a), (b), (c) and (d) is lower than 400 mOsm/kg.

* * * * *